United States Patent [19]

Hanifin, Jr. et al.

[11] 4,173,650
[45] Nov. 6, 1979

[54] CIS-2-BENZOYL-3-HYDROXY-2-ALKENONITRILES AS ANTI-INFLAMMATORY AGENTS

[75] Inventors: John W. Hanifin, Jr., Suffern; David N. Ridge, Grandview, both of N.Y.

[73] Assignee: American Cyanamid Company, Stamford, Conn.

[21] Appl. No.: 957,595

[22] Filed: Nov. 3, 1978

[51] Int. Cl.² ................ A61K 31/275; C07C 121/76
[52] U.S. Cl. .................................... 424/304; 548/247; 260/429 R; 260/465 E; 260/465 F; 260/465 G; 260/465 R; 260/465.6; 260/544 D; 260/570.5 C; 546/230
[58] Field of Search .......... 260/465 F, 465 G, 465 R; 424/304

[56] References Cited
U.S. PATENT DOCUMENTS
3,658,838  4/1972  Kiehne et al. ............ 260/465 F X 4,061,767  12/1977  Ertel et al. ................ 260/465 D X

OTHER PUBLICATIONS

Panizzi, Chemical Abstracts, vol. 42, 559–561 (1948).
Vila et al., Chemical Abstracts, vol. 47, 9940 (1952).
Edwards et al., Chemical Abstracts, vol. 50, 1505 (1956).

*Primary Examiner*—Dolph H. Torrence
*Attorney, Agent, or Firm*—Edward A. Conroy, Jr.

[57]  ABSTRACT

This disclosure describes new compounds and compositions of matter useful as anti-inflammatory agents and as inhibitors of the progressive joint deterioration characteristic of arthritic disease and the methods of meliorating inflammation and of inhibiting joint deterioration in mammals therewith, the novel active ingredients of said compositions of matter being certain substituted cis-2-benzoyl-3-hydroxy-2-alkenonitriles and/or the pharmacologically acceptable cationic salts thereof.

19 Claims, No Drawings

CIS-2-BENZOYL-3-HYDROXY-2-ALKENONITRILES AS ANTI-INFLAMMATORY AGENTS

BRIEF SUMMARY OF THE INVENTION

This invention relates to new organic compounds and, more particularly, is concerned with novel substituted cis-2-benzoyl-3-hydroxy-2-alkenonitriles and the pharmacologically acceptable cationic salts thereof which may be represented by the following structural formula:

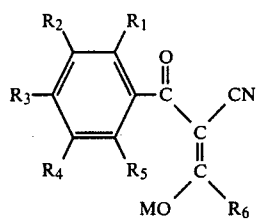

wherein $R_1$, $R_2$, $R_3$, $R_4$ and $R_5$ are each individually selected from the group consisting of hydrogen, halogen, alkyl having from 1 to 4 carbon atoms, alkoxy having from 1 to 4 carbon atoms, trifluoromethyl and trichloromethyl with the proviso that at least two of $R_1$, $R_2$, $R_3$, $R_4$ and $R_5$ must be hydrogen but $R_1$, $R_2$, $R_3$, $R_4$ and $R_5$ may not all be hydrogen; $R_6$ is alkyl having from 1 to 4 carbon atoms; and M is hydrogen or a pharmaceutically acceptable cation. The useful pharmaceutically acceptable salts of the compounds of the above structural formula wherein M is hydrogen are those with pharmacologically acceptable metal cations, ammonium or amine cations. Preferred metal cations are those derived from the alkali metals, e.g. lithium, sodium and potassium, and from the alkaline earth metals, e.g. magnesium and calcium, although cationic forms of other metals, e.g. aluminum, zinc, iron and in particular copper, are within the scope of the invention.

Pharmacologically acceptable amine cations are those derived from primary, secondary or tertiary amines such as mono- di- or trimethylamine, ethylamine, dibutylamine, triisopropylamine, N-methylhexylamine, decylamine, dodecylamine, allylamine, crotylamine, cyclopentylamine, dicyclohexylamine, mono- or dibenzylamine, α- or β-phenylethylamine, ethylenediamine, diethylenetriamine, and arylaliphatic amines containing up to and including 18 carbon atoms, as well as heterocyclic amines, e.g. piperidine, morpholine, pyrrolidine, piperazine and lower alkyl derivative thereof, e.g. 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g. mono-, di-, or triethanolamine, ethyldiethanolamine, N-butylethanolamine, 2-amino-1-butanol, 2-amino-2-ethyl-1,3-propanediol, 2-amino-2-methyl-1-propanol, tris(hydroxy-methyl)amino methane, N-phenylethanolamine, N-(p-tert-amylphenyl)diethanolamine, and the like. Suitable alkyl and alkoxy groups contemplated by the present invention may be, for example, methyl, ethyl, isopropyl, sec-butyl, methoxy, ethoxy, n-propoxy, isobutoxy, etc., whereas halogen is exemplified by fluoro, chloro and bromo.

The cis-2-benzoyl-3-hydroxy-2-alkenonitriles of the present invention may exist in other tautomeric forms as follows:

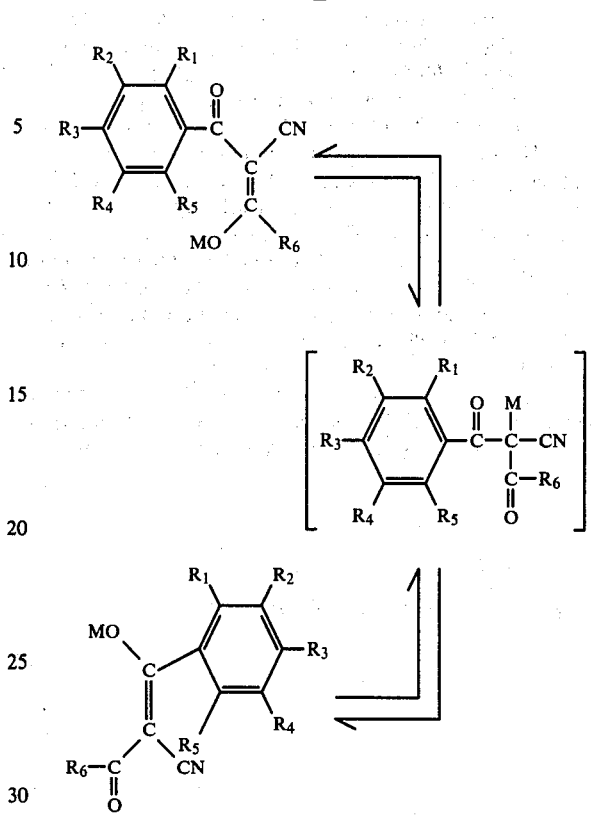

DETAILED DESCRIPTION OF THE INVENTION

Several procedures exist for the attachment of the acyl fragment to a benzoylacetonitrile side chain. The first involves direct acylation of the benzoylacetonitrile anion (1) with an acyl halide (2) in an appropriate solvent to provide the product (3) as set forth in the following reaction scheme wherein Me is a metal cation as hereinabove defined, X is chloro or fluoro, and $R_1$, $R_2$, $R_3$, $R_4$, $R_5$ and $R_6$ are as hereinabove defined. The enolate anions (1)

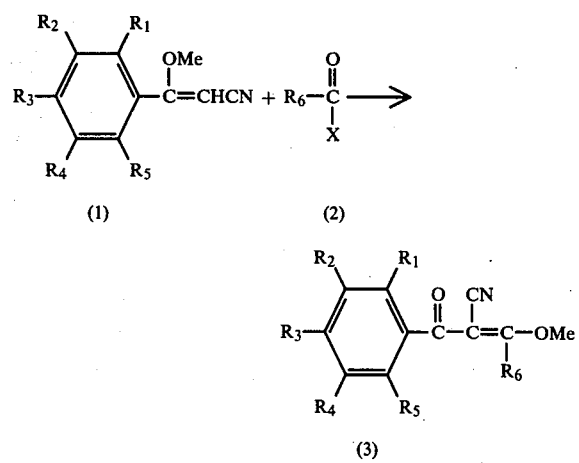

are prepared by the treatment of the benzoylacetonitrile with the appropriate base in an inert solvent. This enolate may be generated in situ and acylated with (2) in the same solvent or may be isolated and reacted in a different solvent system. When Me represents sodium where (1) has been generated by treatment of the benzoylacetonitrile with sodium hydride, sodium amide, sodium methoxide, etc. and X represents chlorine, yields of (3) are low with undesired side products sometimes predominating. Preferably, the benzoylacetonitrile is dissolved in diethyl ether and one equivalent of thallium (I) ethoxide is added. The stable enolate (1), where Me is thallium, precipitates and may be collected by filtration, dried and stored indefinitely. Suspension of (1) in an inert solvent such as ether, tetrahydrofuran, dioxane, etc. at room temperature and the treatment of same with an acyl fluoride (2) causes precipitation of thallium (I) fluoride. This is removed by filtration and the product is extracted from the filtrate.

Another approach involves addition of the acyl fragment as a hydrolyzable portion to yield (5) wherein $R_1$, $R_2$, $R_3$, $R_4$ and $R_5$ are as hereinabove defined. This may be

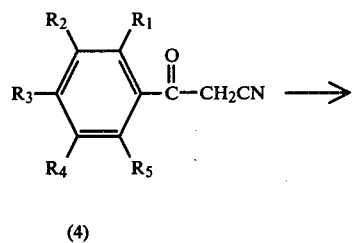

(4)

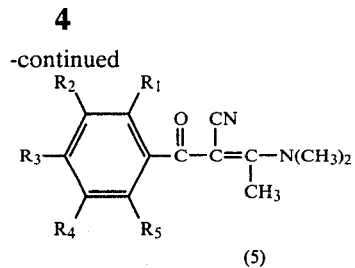

(5)

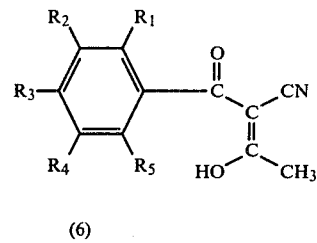

(6)

performed by treatment of the benzoylacetonitrile (4) with N,N-dimethylacetamide dimethylacetal at low temperature in chloroform, methylene chloride, or even as a neat mixture of reagents. Purification yields the condensed product (5). Alternatively, the benzoylacetonitrile (4) is condensed with a trialkyl orthoester (7) in refluxing acetic anhydride as set forth in the following reaction scheme:

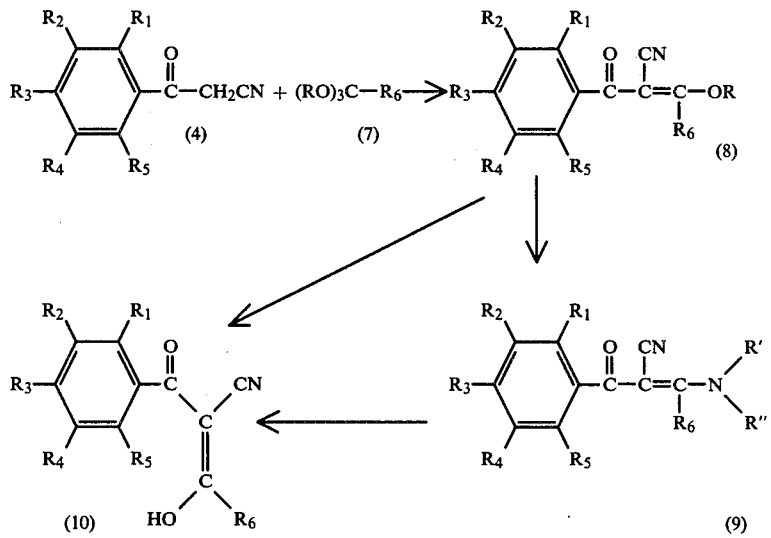

wherein $R_1$, $R_2$, $R_3$, $R_4$, $R_5$ and $R_6$ are as hereinbefore defined, R is alkyl having up to 4 carbon atoms, R' and R" are each hydrogen or alkyl having up to 4 carbon atoms and R' and R" taken together with the associated N(itrogen) is pyrrolidino, piperidino, morpholino, thiomorpholino or N-methylpiperazino. Evaporation of by-products and excess acetic anhydride in vacuo and purification of the product under anhydrous conditions provides (8). Treatment of (8) with ammonia or a primary or secondary amine at steam bath temperature under pressure in a sealed vessel for 8–12 hours then provides (9). Both of these intermediates (8) and (9) may be hydrolyzed under acidic conditions to provide the desired products (10).

A different approach to (10) wherein $R_6$ is methyl or ethyl involves addition of the cyanoacyl fragment to a benzoyl chloride as set forth below wherein $R°$ is methyl or ethyl and $R_1$, $R_2$, $R_3$, $R_4$ and $R_5$ are as hereinabove defined.

A less desirable route to (10) involves that set forth below wherein $R_1$, $R_2$, $R_3$, $R_4$, $R_5$ and $R_6$ are as hereinabove defined.

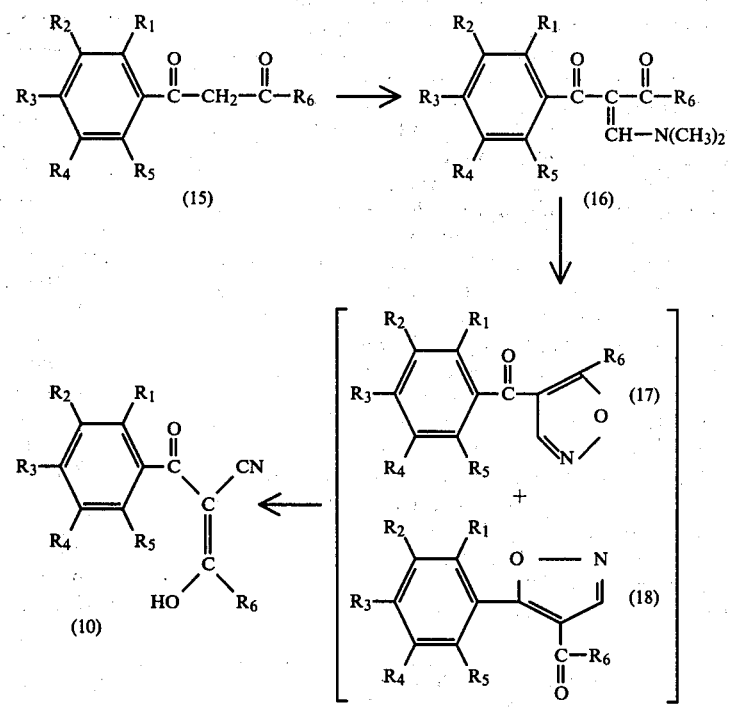

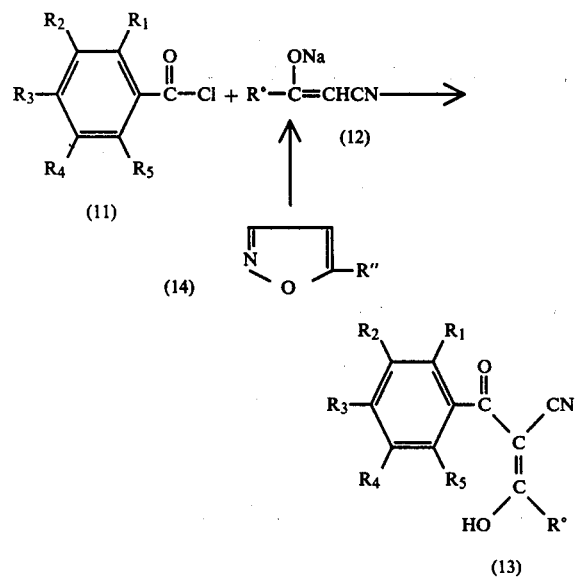

This may be performed by generation of the enolate anion (12) in situ with the 5-alkyl-isoxazole (14) and a base such as sodium hydride or sodium amide and subsequent addition of the benzoyl chloride (11) to affect condensation to provide (13). Alternatively the α-cyanoenolate (12) may be prepared separately in a similar manner as above and isolated. Addition of this enolate to the appropriate benzoyl chloride in ether, tetrahydrofuran, etc. at room temperature or at reflux provides (13).

The acylacetophenone (15) is condensed with N,N-dimethylformamide dimethylacetal at reflux either neat or in solution with an inert solvent such as chloroform or carbon tetrachloride to give the intermediate (16). Treatment of this with hydroxylamine hydrochloride in solvents such as alcohol, dioxane, dimethylformamide or aqueous solutions of the same provides a mixture of products (17) and (18). These are reacted as an unseparated mixture with a strong base such as sodium hydroxide or sodium alkoxide in alcohol and provides the desired product (10) upon acidification.

The novel compounds of the present invention have been found to be highly useful for meliorating inflammation and inhibiting joint deterioration in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gm. to about 7.0 gm. of the active ingredient for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, topical, intra-articular, or subcutaneous route. The antiinflammatory activity of the novel compounds of the present invention was established by the following tests.

(A) Carrageenin-induced edema in the rat

In determining the acute anti-inflammatory activity of the cis-2-benzoyl-3-hydroxy-2-alkenonitriles of the present invention, Royal Hart, Wistar strain rats, ranging in weight from 80 to 90 grams were used. The rats were fasted overnight prior to dosing but had free access to water. The test compounds were administered in aqueous suspension, by gavage, in a volume of 1.7 ml. per 50 grams of rat [corresponds to hydration volume used by Winter, et al., Proc. Soc. Exp. Biol. & Med., 111, 544–547 (1962)]. The phlogistic agent used was carrageenin prepared as a sterile 1% suspension in 0.9% aqueous sodium chloride for routine testing. A volume of 0.05 ml. was injected through a 26 gauge needle into the plantar tissue of the right hind paw. Measurements were made 5 hours after drug administration (4 hours after carrageenin challenge). Volumes of both the normal and carrageenin inflammed feet were determined. The difference between the two measurements is considered to be the increased edema due to the carrageenin administration. Results are expressed as a C/T efficacy ratio (edema of control animals/edema of treated animals). Table I records the results of this test at the indicated dose level with typical compounds of the present invention and demonstrates the anti-inflammatory effect of these compounds in comparison with known anti-inflammatory agents.

Table I

The Effect of Anti-inflammatory Agents on Carrageenin-Induced Edema

| Compound | Number of Rats | C/T Ratio |
|---|---|---|
| Control | 8 | — |
| Aspirin | 8 | 2.86* |
| Cis-2-(m-fluorobenzoyl)-3-hydroxy-crotononitrile | 7 | 1.61* |
| Cis-3-hydroxy-2-p-toluoylcrotononitrile | 8 | 1.41* |
| Cis-3-hydroxy-2-(p-anisoyl)-crotononitrile | 5 | 1.59* |
| Cis-3-hydroxy-2-(o-anisoyl)-crotononitrile | 8 | 1.30* |
| Cis-2-(o-fluorobenzoyl)-3hydroxy-crotononitrile | 8 | 2.18* |
| Cis-3-hydroxy-2-(α,α,α-trifluoro-p-toluoyl)crotononitrile | 3 | 1.97* |

(B) Adjuvant-induced arthritis in the rat

The following test shows the activity of the cis-2-benzoyl-3-hydroxy-2-alkenonitriles of this invention against chronic inflammation in adjuvant induced arthritis which is accompanied by joint destruction. Groups of three Royal Hart, Wistar strain rats weighing $200 \pm 10$ g. each were injected intradermally in the right hind paw with Freund's adjuvant (dried human tubercle bacilli in a mineral oil vehicle) at a dose of 2 mg./kg. of body weight. The test compounds were administered orally in a 1.5% starch vehicle at various doses once daily on days 0 to 13 post challenge. Control rats were treated in a similar manner, but given only starch vehicle. On the 14th and 21st day post challenge the diameter of the injected paw was measured by micrometer caliper. The volume of inflamed paws were estimated from these measurements and the effects of each compound are expressed as percent inhibition of swelling as compared to controls. Table II records the results of these tests conducted with representative compounds of this invention and known anti-inflammatory agents. The active compounds of this invention suppress the progression of the arthritis and associated joint deterioration.

Table II

The Effect of Anti-Inflammatory Agents on Adjuvant Induced Arthritis in Rats

| Compound | Oral Dose (mg./kg.) | Number of Rats | % Inhibition of Swelling Day 14 | % Inhibition of Swelling Day 21 |
|---|---|---|---|---|
| Normal rats | — | — | — | — |
| Adjuvant Controls | — | | 0 | 0 |
| Indomethacin | 2 | 57 | 51* | 24* |
|  | 1 | 54 | 46* | 19* |
|  | 0.5 | 54 | 40* | 20* |
|  | 0.25 | 9 | 30* | 4 |
| Aspirin | 400 | 57 | 73* | 48* |
|  | 200 | 66 | 48* | 27* |
|  | 100 | 63 | 36* | 13 |
|  | 50 | 21 | 23* | 3 |
| Phenylbutazone | 150 | 27 | 75* | 44* |
|  | 75 | 39 | 62* | 28* |
|  | 37.5 | 39 | 56* | 14 |
|  | 18.8 | 21 | 31* | 7 |
| Cis-2-(p-fluorobenzoyl)-3-hydroxycrotononitrile | 25 | 18 | 65* | 30* |
| Cis-2-(p-chlorobenzoyl)-3-hydroxycrotononitrile | 25 | 21 | 58* | 15 |
| Cis-2-(o-chlorobenzoyl)-3-hydroxycrotononitrile | 50 | 9 | 39* | 29 |
| Cis-2-(m-fluorobenzoyl)-3-hydroxycrotononitrile | 50 | 9 | 48* | 37* |
| Cis-2-(3-chloro-o-toluoyl)-3-hydroxycrotononitrile | 50 | 9 | 61* | 17 |
| Cis-3-hydroxy-2-(α,α,α-trifluoro-p-toluoyl)crotononitrile | 25 | 6 | 68* | 5 |

*Statistically significant activity $p = <.05$ by t test

Adjuvant-induced experimental polyarthritis is a specific systemic disease of the rat which shares interesting similarities with rheumatoid arthritis. Specifically the histology of the two diseases bears a remarkable resemblence as shown by C. M. Pearson et al., Am. J. Path. 42, 73 (1963). E. M. Glenn, Am. J. Vet. Res. 27, (116), 339 (1966) has classified adjuvant-induced polyarthritis as a crippling and permanent deformity resulting from diffuse connective tissue involvement areound certain susceptible joints in the rat. Zahiri et al, Can. Med. Ass. J., 101, 269 (1969) have shown that the fusiform swelling of the distal joints is associated with edema, congestion and synovitis including pannus formation, all of which precede the ultimate destruction of bone and cartilage. Furthermore, Zahiri et al., indicate that the cartilage destruction in the joint is due to an invasive pannus which originates in the marginal synovium and extends across the articular surface to erode it. When non-steroidal, anti-inflammatory agents such as indomethacin inhibit arthritic paw swelling, which is composed of inflammatory cell infiltrates, they have also been shown to prevent joint and bone deterioration [see S. Wong et al., J. Pharm. & Exp. Ther. 185, 127 (1973) and G. R. Bobalick et al., Agents and Actions 4, 364 (1974)]. The most pointed reference showing the relationship between arthritis and joint deterioration is an X-Ray analysis of adjuvant arthritis in the rat by Blackham et al., Agents and Actions 7, 145 (1977). In a similar manner, inhibition of the progress of arthritis in paws of rats treated with the compounds of this invention also lessens associated joint deterioration.

(C) Migration inhibitory factor in the guinea pig

Rheumatoid arthritis is a chronic inflammatory disease that is characterized by the migration of lymphocytes, macrophages and polymorphonuclear leukocytes to the sites of inflammation. The migration of lymphocytes and macrophages and their multiplication in situ is one reason for the very large increase in size of the normally thin synovial membrane, the membrane that encloses the joint space. The synovial membrane that has been transformed in this manner, slowly grows over the aricular surfaces and causes the destruction of the articular cartilage and other connective tissue structures of the joint. One of the mechanisms for the destruction of articular cartilage by the synovium is believed to be through the release of various hydrolytic enzymes by the resident macrophages which have been immobilized and activated by migration inhibitory factor (MIF). Macrophages stimulated by MIF are termed "activated macrophages" and undergo the following changes: (a) increased glucose oxidation, (b) increased ruffling of plasma membrane and increased spreading of cells, (c) synthesis and secretion of neutral proteases, (d) release of preformed lysosomal enzymes, (e) decreased migration from a capillary tube. All these effects are associated with an inflammatory situation and it has been demonstrated that MIF is present in the synovial fluid from patients with rheumatoid arthritis. The mechanisms of cartilage destruction can be pictured as follows:

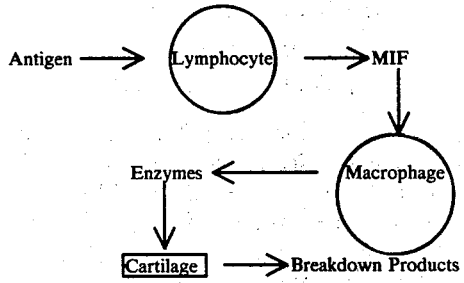

Although the postulated antigen initiating these destructive events in rheumatoid arthritis has not been discovered, the secretion of MIF by lymphocytes and the secretion of enzymes by macrophages as well as the breakdown of cartilage by macrophage enzymes has been demonstrated. Drugs that can therefore block the release of MIF by lymphocytes or the activation of macrophages by MIF should be clinically effective in retarding the destructive joint damage which occurs in rheumatoid arthritis. Drugs can be tested as MIF inhibitors by using the capillary tube migration assay as follows.

Male Hartley guinea pigs, weighing between 300 and 600 grams, are injected intraperitoneally with 25 ml Marcal 52 Oil ® (Humble Oil). Three to four days later, the guinea pigs are sacrificed by decapitation, the peritoneum opened, and the exudate aspirated into a separatory funnel after the addition of 50 ml of cold Hank's solution. This is repeated two times. The oil phase is discarded and the cell supsension is spun down at 1200 r.p.m. for ten minutes. The cells are resuspended in Hank's solution and spun down at 900 r.p.m. for five minutes. This is repeated two times. Viability of the cells is then determined using trypan blue. In all experiments, viability is greater than 90%. The cell concentration is then adjusted to give a 10% packed cell volume by the addition of the appropriate amount of MEM ® (Gibco 109)+15% guinea pig serum. To the medium is added L-glutamine (2 mM), penicillin (100 U/ml) and streptomycin (100 µg/ml. Capillary tubes (1.1–1.5×75 mm, Clay Adams) are filled with cells by capillary action and sealed at one end with a small plug of paraffin. Capillary tubes are centrifuged at 700–800 r.p.m. for five minutes to get approximately 4–5 mm of packed cells at the closed end. The tubes are cut at the cell-fluid interface. Two packed capillary tubes are then transferred to each chamber of the Lexy culture dish (Mini-Lab Co. LLC-4002, Quebec, Canada). The capillaries are held in place using a small amount of silicone grease (Dow Corning) and a cover glass then placed on top of the chamber, making a seal between the cover glass and the chamber using paraffin wax. Chambers are then filled with medium or in medium in which antigen (PPD) or antigen+drug are dissolved, by filling the chamber through the passages. After the addition of medium, the passages are sealed off using silicone. The cells are then incubated at 37° C. for 24 hours. To determine the area of cell migration out of the capillary tube onto the chamber surface, the chambers are projected onto a microscope screen, the area traced onto paper, and then measured using a planimeter. The antigen, PPD, inhibits the migration of macrophages by approximately 50%. Drugs that reverse this inhibition by greater than 15% are considered active. Table III lists the results of this direct MIF assay at the indicated dose level with typical compounds of the present invention.

Table III

The Effect of Anti-Inflammatory Agents on Migration Inhibitory Factor

| Compound | Dose | % Reversal* | #Actives** Total Tests |
|---|---|---|---|
| Cis-2-(p-fluorobenzoyl)-3-hydroxycrotononitrile | $5 \times 10^{-5}$M | 48 | 4/4 |
| Cis-2-(p-bromobenzoyl)-3-hydroxycrotononitrile | 10 µg./ml. | 25 | 2/3 |
| Cis-2-(o-anisoyl)-3-hydroxycrotononitrile | $5 \times 10^{-5}$M | 18 | 4/5 |
| Cis-2-(3-chloro-o-toluoyl)-3-hydroxycrotononitrile | $5 \times 10^{-5}$M | 16 | 3/5 |

*Percent reversal of inhibition $= \frac{c - b}{a - b}$
wherein a = cells with no addition, b = cells + antigen, and c = cells + antigen + drug.
**Ratio is the number of tests wherein the percent reversal of inhibition =15%.

Compositions according to the present invention having the desired clarity, stability and adaptability for parenteral and intra-articular use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Althought the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chlorophenyl-$\alpha$-glycerol ether, methyl and propyl parabens, and thimerosal. As a practical matter it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The cis-2-benzoyl-3-hydroxy-2-alkenonitriles are equally adapted to intravenous administration when diluted with water or diluents employed in intravenous therapy such as isotonic glucose in appropriate quantities. For intravenous use, initial concentrations down to about 0.05 to 0.25 mg./ml. of active compound are sitisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The invention will be described in greater detail in conjunction with the following specific examples.

EXAMPLE 1

3-Dimethylamino-2-(p-fluorobenzoyl)crotononitrile

To a solution of 1.6 g. of p-fluorobenzoylacetonitrile [Pihl et al., Reakts. Sposobnost Org. Soedin. Tartu. Gos. Univ., 5 (1), 27, (1968)] in 30 ml. of chloroform, cooled to $-10°$ C., is added 1.4 g. of N,N-dimethylacetamide dimethylacetal. The reaction mixture is stirred at $-10°$ C. for 2 hours and the evaporated in vacuo to an oil. This oil is dissolved in 150 ml. of benzene and filtered through magnesol. The filtrate is evaporated to 50 ml. and petroleum ether is added to effect crystallization. The product is collected by filtration and then recrystallized from benzene-petroleum ether with charcoal treatment giving the desired product.

EXAMPLE 2

Cis-2-(p-fluorobenzoyl)-3-hydroxycrotononitrile

To a solution of 6.7 g. of p-fluorobenzoylacetonitrile in 100 ml. of chloroform, cooled to 0° C., is added 7 ml. of N,N-dimethylacetamide dimethylacetal. The reaction mixture is stirred in an ice bath for 2 hours and then at room temperature for 16 hours. The solution is evaporated in vacuo to an oil. This oil is dissolved in chloroform, filtered through magnesol and then evaporated to an oil. This oil is dissolved in 100 ml. of methanol and 20 ml of 1N hydrochloric acid is added. The reaction mixture is heated on a steam bath for 25 minutes, cooled and the precipitate is collected. The solid is recrystallized from 50 ml. of cyclohexane, giving the desired product.

EXAMPLE 3

3,4-Difluoroacetophenone

Dry aluminum chloride (26 g., 0.19 mole) is added to a 250 ml. three-neck flask under argon and the flask is cooled in ice. Acetyl chloride (14 ml. 0.19 mole) is then added dropwise, followed by 20 g. (0.18 mole) of o-difluorobenzene. The ice bath is removed and the reaction is slowly warmed and eventually held at 100° for 3.5 hours. The hot reaction solution is then poured onto ice and extracted with ether. The organic extracts are washed with aqueous sodium bicarbonate and evaporated. The dark residue (23 g.) is distilled at 39°/0.1 mm to provide 20 g. (73%) of colorless 3,4-difluoroacetophenone (mp. ca. 20°). Similarly prepared is 2,5-difluoroacetophenone.

EXAMPLE 4

3,4-Difluorophenacyl bromide

To a solution of 10.1 g. (0.065 mole) of 3,4-difluoroacetophenone in 100 ml. of glacial acetic acid was added 3.4 ml. (0.065 mole) of bromine dropwise. When the addition was complete the solution was stirred for 0.5 hr. and then stripped to dryness under reduced pressure. The residue was dissolved in chloroform and washed with aqueous sodium bicarbonate. Evaporation of the organic phase provided 14.8 g. (97%) of colorless liquid product. Similarly prepared were 2,4-dichlorophenacyl bromide, o-ethylphenacyl bromide, p-isopropylphenacyl bromide, m-isobutylphenacyl bromide, 3,4-dimethylphenacyl bromide, m-ethoxyphenacyl bromide, p-isopropoxyphenacyl bromide, 3,4-diethoxyphenacyl bromide, and 2,5-difluorophenacyl bromide.

EXAMPLE 5

3,4-difluorobenzoylacetonitrile

A solution of 13.2 g. (0.056 mole) of 3,4-difluorophenacyl bromide was dissolved in 100 ml. of ethanol and cooled to 5° C. in ice. A solution of 7.6 g. (0.16 mole) of sodium cyanide in 40 ml. of water was added dropwise over 0.5 hr. and the reaction is stirred for an additional one hour. At that time, the mixture was diluted with 100 ml. of water and filtered through Celite ®. Acidification of the filtrate gave a cloudy mixture which was extracted with methylene chloride. The organic phase was dried, filtered through Magnesol ® and evaporated. Recrystallization of the residue from carbon tetrachloride provides 5.3 g. (52%) of colorless solid, m.p. 74°–75° C. Similarly prepared were 2,4-dichlorobenzoylacetonitrile, o-ethylbenzoylacetonitrile, p-isopropylbenzoylacetonitrile, m-isobutylbenzoylacetonitrile, 3,4-dimethylbenzoylacetonitrile, m-ethoxybenzoylacetonitrile, p-isopropoxybenzoylacetonitrile, 3,4-diethoxybenzoylacetonitrile, and 2,5-difluorobenzoylacetonitrile.

EXAMPLE 6 p-Fluorobenzoylacetonitrile, thallium (I) salt

A suspension of 10 g. of p-fluorobenzoylacetonitrile in 200 ml. of dry diethyl ether is stirred at room temperature while 17.2 g. of neat thallium (I) ethoxide is slowly added. The resulting reaction mixture is stirred for one hour at room temperature and then filtered. The collected precipitate is washed with diethyl ether and air dried whereby there is obtained 23.7 g. (99% yield) of the thallium (I) salt of p-fluorobenzoylacetonitrile which may be stored at room temperature.

In a similar manner, the thallium (I) salts tabulated below were prepared.

| Example No. | Thallium (I) salts |
|---|---|
| 7 | m-Chlorobenzoylacetonitrile, thallium (I) salt |
| 8 | p-Bromobenzoylacetonitrile, thallium (I) salt |
| 9 | o-Bromobenzoylacetonitrile, thallium (I) salt |
| 10 | 2,4-Dichlorobenzoylacetonitrile, thallium (I) salt |
| 11 | 3,4-Difluorobenzoylacetonitrile, thallium (I) salt |
| 12 | o-Ethylbenzoylacetonitrile, thallium (I) salt |
| 13 | p-Isopropylbenzoylacetonitrile, thallium (I) salt |
| 14 | m-Isobutylbenzoylacetonitrile, thallium (I) salt |
| 15 | 3,4-Dimethylbenzoylacetonitrile, thallium (I) salt |
| 16 | m-Ethoxybenzoylacetonitrile, thallium (I) salt |
| 17 | p-Isopropoxybenzoylacetonitrile, thallium (I) salt |
| 18 | 3,4-Diethoxybenzoylacetonitrile, thallium (I) salt |

EXAMPLE 19

Cis-2-(p-fluorobenzoyl)-3-hydroxycrotononitrile

To a suspension of 2.2 g. of p-fluorobenzoylacetonitrile, thallium (I) salt in 20 ml. of tetrahydrofuran is added 2 ml. of acetyl fluoride with stirring at room temperature. After one hour, another 2 ml. of acetyl fluoride is added, followed by 2 ml. more after twelve hours. Twelve hours later, the precipitated thallium (I) fluoride is removed by filtration and the filtrate is evaporated to dryness. The off-white residue is recrystallized from ethanol to provide the cis-2-(p-fluorobenzoyl)-3-hydroxycrotononitrile.

EXAMPLE 20

Cis-2-(p-bromobenzoyl)-3-hydroxy-2-pentenonitrile

A suspension of 5.0 g. of p-bromobenzoylacetonitrile, thallium salt in 30 ml. of tetrahydrofuran is treated with an excess of propionyl fluoride. After 15 hours, the precipitate is filtered off and the filtrate is stripped to dryness. The residue is dissolved in chloroform and extracted with aqueous sodium bicarbonate. The aqueous phase is acidified and the product is extracted with chloroform. The title compound is obtained after column chromatography.

In a similar manner the acid fluorides listed below were reacted with the appropriately substituted benzoylacetonitrile thallium salts to provide the compounds tabulated below.

| Example No. | Product | Acid Fluoride | Thallium Salt from Example No. |
|---|---|---|---|
| 21 | Cis-2-(m-chlorobenzoyl)-3-hydroxy-2-hexenonitrile | Butyryl Fluoride | 7 |
| 22 | Cis-2-(p-bromobenzoyl)-3-hydroxy-2-pentenonitrile | Propionyl Fluoride | 8 |
| 23 | Cis-2-(o-bromobenzoyl)-3-hydroxy-4-methyl-2-pentenonitrile | Isobutyryl Fluoride | 9 |
| 24 | Cis-2-(2,4-dichlorobenzoyl)-3-hydroxy-2-heptenonitrile | Valeryl Fluoride | 10 |
| 25 | Cis-2-(3,4-difluorobenzoyl)-3-hydroxy-5-methyl-2-hexenonitrile | Isovaleryl Fluoride | 11 |
| 26 | Cis-2-(o-ethylbenzoyl)-3-hydroxy-4-methyl-2-hexenonitrile | 2-Methylbutyryl Fluoride | 12 |
| 27 | Cis-2-(p-isopropylbenzoyl)-3-hydroxy-4,4-dimethyl-2-pentenonitrile | Pivalyl Fluoride | 13 |
| 28 | Cis-2-(m-isobutylbenzoyl)-3-hydroxy-2-pentenonitrile | Propionyl Fluoride | 14 |
| 29 | Cis-2-(3,4-dimethylbenzoyl)-3-hydroxyhexenonitrile | Butyryl Fluoride | 15 |

-continued

| Example No. | Product | Acid Fluoride | Thallium Salt from Example No. |
| --- | --- | --- | --- |
| 30 | Cis-2-(m-ethoxybenzoyl)-3-hydroxy-4-methyl-2-pentenonitrile | Isobutyryl Fluoride | 16 |
| 31 | Cis-2-(p-isopropoxybenzoyl)-3-hydroxy-2-heptenonitrile | Valeryl Fluoride | 17 |
| 32 | Cis-2-(3,4-diethoxybenzoyl)-3-hydroxy-5-methyl-2-hexenonitrile | Isovaleryl Fluoride | 18 |

EXAMPLE 33

Cis-2-(p-chlorobenzoyl)-3-hydroxycrotonitrile

To a mixture of 68.5 g. of p-chlorobenzonitrile and 24.0 g. of sodium hydride (50% in mineral oil) in 250 ml. of ether is added, 26.1 ml. of acetonitrile and 2 ml. of isopropanol. The mixture is stirred and refluxed on a steam bath for 6 hours and then stirred overnight at room temperature. A 5 ml. portion of methanol and 250 ml. of water are added. The ether is boiled away on a steam bath and the mixture is filtered. The solid is dissolved in warm ethyl acetate and filtered. The filtrate is evaporated to a solid giving β-amino-4-chlorocinnamonitrile.

A 94.68 g. portion of β-amino-4-chlorocinnamonitrile is suspended in 250 ml. of water. A 50 ml. portion of concentrated hydrochloric acid is added and the mixture is stirred overnight. The solid is collected and stirred for 4 hours in a mixture of 250 ml. of water, 250 ml. of 2B ethanol and 50 ml. of concentrated hydrochloric acid. The reaction mixture is evaporated and the solid is taken up in methylene chloride and passed through magnesol. The filtrate is evaporated on a steam bath with the addition of hexanes giving crystals of p-chlorobenzoylacetonitrile.

A 9.0 g. portion of p-chlorobenzoylacetonitrile in 100 ml. of chloroform is reacted with 10 ml. of N,N-dimethylacetamide dimethylacetal as described in Example 2, giving the desired product.

EXAMPLE 34

Cis-2-(o-chlorobenzoyl)-3-hydroxycrotononitrile

A 150 ml. portion of ammonia is condensed in a reaction flash and a small piece of sodium is added. The blue color is discharged by the addition of ferric chloride and 3.22 g. of sodium are added. After the cooler is discharged 5.75 ml. of acetonitrile in 10 ml. of ether are added. The reaction is cooled in a dry ice-acetone bath and 13.3 g. of 2-chlorobenzonitrile in 25 ml. of tetrahydrofuran are added dropwise. The ammonia is allowed to evaporate, the solvent is blown off with nitrogen and water is added. The mixture is extracted with methylene chloride. The organic extracts are dried over sodium sulfate and filtrate through magnesol. The filtrate is evaporated with the addition of hexanes giving β-amino-2-chlorocinnamonitrile as a white crystalline solid.

A 45 ml. portion of 1 N hydrochloric acid is added to the β-amino-2-chlorocinnamonitrile and the reaction is stirred overnight. The solid is collected, washed with water, dried, taken up in methylene chloride and passed through magnesol. The filtrate is evaporated on a steam bath with the addition of hexanes giving o-chlorobenzoylacetonitrile as a white crystalline solid.

A 4.4 g. portion of o-chlorobenzoylacetonitrile in 50 ml. of chloroform is reacted with 5 ml. of N,N-dimethylacetamide dimethylacetal as described in Example 2, giving the desired product.

EXAMPLE 35

Cis-2-(m-fluorobenzoyl)-3-hydroxycrotononitrile

To a solution of 4.7 g. of m-fluorobenzoylacetonitrile [Pihl, et al., Reakts. Sposabnost. Org. Soedin. Tartu. Gos. Univ., 5 (1), 27 (1968)] in 50 ml. of chloroform, cooled in an ice bath, is added 5 ml. of N,N-dimethylacetamide dimethylacetal. The reaction mixture is stirred at 0° C. for 2 hours then at room temperature for 16 hours. The solution is evaporated in vacuo to an oil. The oil is dissolved in 50 ml. of methanol and 15 ml. of 1 N hydrochloric acid is added. The reaction mixture is heated on a steam bath for 30 minutes and then vaporated in vacuo to an oil. This oil is added to 75 ml. of benzene and extracted three times with a saturated solution of sodium bicarbonate. The combined aqueous phase is washed with benzene, acidified with concentrated hydrochloric acid and the precipitates is collected and recrystallized from isopropanol with charcoal treatment giving the desired product.

EXAMPLE 36

Cis-2-(o-fluorobenzoyl)-3-hydroxycrotononitrile 9.8 g. portion of o-fluorobenzoylactonitrile [Dorsch et al., J. A. C. S. 54, 2960 (1932)] in 100 ml. of chloroform is cooled in an ice-water bath. A 10 ml. portion of N,N-dimethylacetamide dimethylacetal is added and the mixture is stirred in an ice bath for 2 hours and then at room temperature overnight. The mixture is evaporated to an oil, dissolved in 50 ml. of methanol, acidified with 20 ml. of 1 N hydrochloric acid, heated on a steam bath for ½ hour and evaporated to an oil. A 100 ml. portion of chloroform and 100 ml. of saturated aqueous sodium bicarbonate solution are added. The mixture is shaken and the organic phase is again extracted with saturated aqueous sodium bicarbonate solution. The aqueous phases are washed with chloroform, acidified with concentrated hydrochloric acid and the solid is collected, washed with water and recrystallized from hot isopropanol with charcoal treatment giving the desired product.

EXAMPLE 37

Cis-2-(3-chloro-o-toluoyl)-3-hydroxycrotononitrile

A 4.5 g. portion of potassium tertiary butoxide is added to 700 ml. of ether and then cooled in an ice-salt bath. To this is added, over 15 minutes, a mixture of 60.0 g. of 3-chloro-2-methylbenzonitrile and 22.0 ml. of acetonitrile in 300 ml. of ether. The mixture is stirred in the ice bath for ½ hour, allowed to warm to room temperature and then stirred for one hour. This mixture is poured into one liter of water and the layers are separated. The aqueous phase is extracted with ether and the ether layers are combined, washed four times with water and dried over magnesium sulfate. The crystals which form on evaporation are collected and recrystallized from 200 ml. of hot benzene giving 16.0 g. of β-amino-3-chloro-2-methylcinnamonitrile.

An 11.0 g. portion of the above product is added to 150 ml. of methanol and heated to solution on a steam bath. A 50 ml. portion of 1 N hydrochloric acid is added and the mixture is heated on a steam bath for 3 hours. The mixture is cooled, 30 ml. of water are added, the precipitate is collected and air dried. This solid is recrystallized from 80 ml. of hot methanol with charcoal treatment giving 7.8 g. of 3-chloro-2-methylbenzoylacetonitrile.

A 5.4 g. portion of the above ketone in 75 ml. of chloroform is reacted with 60 ml. of N,N-dimethylacetamide dimethylacetal as described in Example 2, to give the desired product.

EXAMPLE 38

Cis-3-hydroxy-2-(p-toluoyl)crotonitrile

To a solution of 10 g. of α-bromo-p-methyl acetophenone in 50 ml. of ethanol in an ice bath is added dropwise a solution of 6.4 g. of sodium cyanide in 30 ml. of water, at a rate so that the temperature is maintained at 25°-30° C. The mixture is then stirred at room temperature for 2 hours, drowned in 600 ml. of water and filtered through celite. The filtrate is acidified to pH 5 with acetic acid, allowed to stand 10 minutes and then filtered. The solid is dissolved in 100 ml. of boiling benzene, magnesium sulfate is added together with charcoal and the mixture is filtered. A 400 ml. portion of hexane is added to the filtrate and the mixture is cooled giving 3.0 g. of p-methylbenzoylacetonitrile.

A 2.6 g. portion of p-methylbenzoylacetonitrile in 30 ml. of chloroform is cooled in an ice bath. A 3 ml. portion of N,N-dimethylacetamide dimethylacetal is added and the mixture is allowed to stand in an ice bath for 2 hours and then at room temperature for 48 hours. The mixture is evaporated to an oil which is dissolved in 20 ml. of methanol. A 3 ml. portion of 1 N hydrochloric acid is added and the mixture is heated on a steam bath for ½ hour and evaporated to a dark oil. This oil is dissolved in 75 ml. of benzene and extracted with three 50 ml. portions of saturated aqueous sodium bicarbonate. The combined aqueous phases are washed with benzene and acidified with concentrated hydrochloric acid. The precipitate is collected and recrystallized from 20 ml. of hot isopropanol with charcoal treatment, giving the desired product.

EXAMPLE 39

Cis-3-hydroxy-2-(o-anisoyl)crotononitrile

A 10.0 g. portion of α-bromo-o-methoxyacetophenone is suspended in 50 ml. of ethanol. A solution of 6.4 g. of sodium cyanide in 30 ml. of water is added as described in Example 38. Following the procedure of Example 38, there is obtained o-methoxybenzoylacetonitrile.

A 3.1 g. portion of o-methoxybenzoylacetonitrile is added to 50 ml. of chloroform cooled in an ice bath. A 3.5 ml. portion of dimethylacetamide dimethylacetal is added and the mixture is stirred in an ice bath for 2 hours and then at room temperature overnight. The mixture is evaporated to an oil which is dissolved in 25 ml. of methanol. A 5 ml. portion of 1 N hydrochloric acid is added and the mixture is heated on a steam bath for ½ hour and then evaporated to an oil. This oil is dissolved in 50 ml. of benzene. A 50 ml. portion of saturated aqueous sodium bicarbonate solution is added forming two layers. The benzene layer is extracted with two 50 ml. portions of saturated aqueous sodium bicarbonate solution. The aqueous phases are combined, washed twice with 50 ml. of benzene and acidified with concentrated hydrochloric acid. The solid is collected, washed with water and recrystallized from hot isopropanol, with charcoal treatment, giving the desired product.

EXAMPLE 40

Cis-3-hydroxy-2-(p-methoxybenzoyl)crotononitrile

A 25.0 g. portion of α-bromo-p-methoxyacetophenone is suspended in 125 ml. of ethanol. A solution of 16.0 g. of sodium cyanide in 75 ml. of water is added, using an ice-water bath to keep the temperature at 25°-30° C. The mixture is stirred for 45 minutes at room temperature. A total of 1.2 liters of water is added in 200 ml. increments with filtration through celite until no more precipitate forms. The filtrate is acidified to pH 5 with acetic acid. The solid is collected, washed with water, dried and recrystallized from benzene giving p-methoxybenzoylacetonitrile.

A 4.7 g. portion of p-methoxybenzoylacetonitrile is added to 50 ml. of chloroform, cooled in an ice bath. A 5 ml. portion of N,N-dimethylacetamide dimethylacetal is added and the mixture is stirred in an ice bath for 2 hours and then at room temperature overnight. The mixture is evaporated to an oil which is dissolved in 25 ml. of methanol. A 5 ml. portion of 1 N hydrochloric acid is added, the mixture is heated on a steam bath for ½ hour and then evaporated to an oil. A 70 ml. portion of saturated aqueous sodium bicarbonate solution and 70 ml. of benzene are added and the mixture separates into two layers. The benzene layer is extracted twice with saturated aqueous sodium bicarbonate solution. The aqueous phases are combined, washed twice with benzene, acidified with 12 N hydrochloric acid and the solid is collected. This solid is recrystallized from 50 ml. of hot isopropanol with charcoal treatment giving the desired product.

EXAMPLE 41

Cis-3-hydroxy-2-(α,α,α-trifluoro-p-toluoyl)crontononitrile

An 8.0 g. portion of diisopropylamine in 100 ml. of ether is cooled to 0° C. under argon. A solution of 31.5 ml. of 2.5 M n-butyllithium in hexane is added dropwise and the reaction is further cooled to −10° C. A 5.94 g. portion of 5-methylisoxazole is then added dropwise and the mixture is stirred for ½ hours. A 15.0 g. portion of p-trifluoromethylbenzoylchloride is added while the reaction is held at 0° C. The mixture is allowed to warm to room temperature and stand for 18 hours. The reaction is quenched with water, acidified with dilute hydrochloric acid and extracted with ether. The ether phase is treated with aqueous sodium carbonate producing three phases. The dark middle phase is isolated, acidified and extracted with chloroform. The extract is dried, filtered and evaporated. The residue is recrystallized from ethanol-hexane giving the desired compound.

EXAMPLE 42

Cyanoacetone, sodium salt

A solution of 0.174 mole of sodium ethoxide is prepared by dissolving 4.0 g. of sodium in 200 ml. of absolute ethanol. A neat sample of 15 ml. (0.184 mole) of 5-methylisoxazole is then added dropwise as a colorless precipitate forms. When the addition is complete, the mixture is cooled in an ice bath and then filtered. The precipitate is collected, and washed with hexane, yielding 14.0 g. of colorless product.

EXAMPLE 43

Cis-3-hydroxy-2-(α,α,α-trifluoro-m-toluoyl)-crotononitrile

A mixture of 5.0 g. (48 mmole) of cyanoacetone, sodium salt in 20 ml. of tetrahydrofuran is stirred at room temperature as a solution of 3.3 g. (16 mmole) of m-trifluoromethylbenzoyl chloride in 5 ml. of tetrahydrofuran is added. The reaction is heated to reflux for 2 hours and the solvent is then evaporated. The residue is acidified and extracted with chloroform. Evaporation of the organic phase provides 4.5 g. of an orange solid which is recrystallized from chloroform to provide 2.4 g. of the title compound.

EXAMPLE 44

1-Cyano-2-butanone, sodium salt

A solution of 0.174 moles of sodium ethoxide is prepared by dissolving 4.0 g. of sodium in 200 ml. of absolute ethanol. A neat sample of 5-ethylisoxazole (17.9 g., 0.185 mole) is then added. The reaction is stirred for one hour as a colorless precipitate forms. The mixture is cooled in an ice bath and filtered. The precipitate is washed with hexane and air dried, yielding the title compound.

EXAMPLE 45

Cis-2-(p-bromobenzoyl)-3-hydroxy-2-pentenonitrile

A mixture of 3.0 g. (25 mmole) of 1-cyano-2-butanone, sodium salt in 20 ml. of tetrahydrofuran is stirred as a solution of (8.6 mmole) of p-bromobenzoyl chloride in 6 ml. of tetrahydrofuran is added. The reaction is heated to reflux for 3 hours, then cooled and the solvent evaporated. The residue is acidified and extracted with chloroform. The organic phase is extracted twice with aqueous sodium bicarbonate which in turn is acidified and extracted again with chloroform. The organic phase is dried and evaporated to yield the title compound.

EXAMPLE 46

Cis-2-(α,α,α-trichloro-p-toluoyl)-3-hydroxy-crotononitrile

In the manner described in Example 41, reaction of 5-methylisoxazole with p-trichloromethylbenzoyl chloride provides the corresponding cis-2-(p-trichloromethylbenzoyl)-3-hydroxy-crotononitrile.

EXAMPLE 47

Preparation of the 50 mg. Tablets

| Per Tablet | | Per 10,000 Tablets |
|---|---|---|
| 0.050 gm. | Cis-2-(p-fluorobenzoyl)-3-hydroxycrotononitrile | 500 gm. |
| 0.080 gm. | Lactose | 800 gm. |
| 0.010 gm. | Corn Starch (for Mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The cis-2-(p-fluorobenzoyl)-3-hydroxycrotononitrile, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 48

Preparation of Oral Suspension

| Ingredient | Amount |
|---|---|
| Cis-2-(p-bromobenzoyl)-3-hydroxy-2-pentenonitrile | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs ad | 100 ml. |

The sorbitol solution is addeed to 40 ml. of distilled water and the cis-2-(p-bromobenzoyl)-3-hydroxy-2-pentenonitrile is suspended therein. The saccharin, sodium benzoate, flavor and dye are added and dissolved. The volume is adjusted to 100 ml. with distilled water. Each ml. of syrup contains 5 mg. of cis-2-(p-bromobenzoyl)-3-hydroxy-2-pentenonitrile.

EXAMPLE 49

Preparation of Parenteral Solution

In a solution of 700 ml. of propylene glycol and 200 ml. of water for injection is suspended 20.0 grams of Cis-3-hydroxy-2-(α,α,α-trifluoro-p-toluoyl)crotononitrile with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 50

Preparation of Topical Cream

| Ingredient | Amount |
|---|---|
| Cis-2-(2-methyl-4-isopropoxybenzoyl)-3-hydroxy-4-methyl-2-pentenonitrile | |
| Ethoxylated stearyl alcohol | 10.0% |
| Benzyl alcohol | 0.9% |
| Isopropyl palmitate | 5.0% |
| Sorbitol solution (USP) | 5.0% |
| Glycerin | 5.0% |
| Lactic acid qs to pH 4.0–5.0 | |
| Water | 100.0% |

The ethoxylated stearyl alcohol and isopropyl palmitate are heated to liquifying temperature. About 95% of the total volume of water is placed in a separate container followed by the glycerin and sorbitol solution. This aqueous mixture is brought to a boil and then cooled to 60°–75° C. The cis-2-(2-methyl-4-isopropoxybenzoyl)-3-hydroxy-4-methyl-2-pentenonitrile is added to the wax phase and the mixture is stirred until a clear solution is obtained. The benzyl alcohol is added and dissolved in the wax phase. The water phase is passed through a screen into the wax phase while maintaining agitation. Both phases are kept at about the same temperature during transfer. The mixture is cooled while agitation is continued. At a temperature of 50°–55° C. the balance of the water is added. The pH is adjusted to 4.0–5.0 with lactic acid. The batch is cooled with minimum agitation until the cream sets in its final form.

EXAMPLE 51

Preparation of Intra-articular Product

| Ingredient | Amount |
|---|---|
| Cis-2-(2-methoxy-4-trifluoromethylbenzoyl)-3-hydroxy-2- heptenonitrile | 2–20 mg. |
| NaCl (physiological saline) | 0.9% |
| Benzyl alcohol N.F. | 0.9% |
| Sodium carboxymethylcellulose | 1–5% |
| pH adjusted to 5.0–7.5 | |
| Water for injection qs ad | 100% |

EXAMPLE 52

Preparation of Injectable Depo Suspension

| Ingredient | % W/V |
|---|---|
| Cis-2-(3,4-difluorobenzoyl)-3-hydroxy-4,4-dimethyl-2-pentenonitrile | 0.05–5 |
| Polysorbate 80 USP | 0.2 |
| Polyethylene glycol 4000 USP | 3.0 |
| Sodium chloride USP | 0.8 |
| Benzyl alcohol N.F. | 0.9 |
| HCl to pH 6–8 | qs |
| Water for injection qs ad | 100.0 |

EXAMPLE 53

2,5-Dichloro-β-aminocinnamonitrile

To a dry 250 ml. three-neck flask is added 30 ml. of hexane under argon, followed by 2.2 g. (46 mmole) of 50% sodium hydride in oil. The mixture is stirred for 5 minutes, the hexane is siphoned off and replaced by 30 ml. of ether. A solution of 7.0 g. (41 mmole) of 2,5-dichlorobenzonitrile, 2.4 ml. (46 mmole) of acetonitrile and 0.4 ml. (4 mmole) of t-butanol diluted to 45 ml. with ether is then added dropwise to the stirred sodium hydride mixture. When the addition is complete, the mixture is heated to reflux overnight. After 24 hours, 40 ml. of water is cautiously added and the ether phase is separated. This solution is dried and evaporated to yield 6.4 g. of off white solid. This residue is dissolved in chloroform, filtered through a magnesol pad and the filtrate is concentrated on the steam bath and diluted with hexane. Upon cooling, 5.0 g. of colorless product precipitated.

Similarly prepared is 3,5-dimethoxy-β-aminocinnamonitrile; 3,4,5-trimethoxy-β-aminocinnamonitrile; and 2,4,6-trimethyl-β-aminocinnamonitrile.

EXAMPLE 54

2,5-Dichlorobenzoylacetonitrile

A two-phase mixture of 5.0 g. of 2,5-dichloro-β-aminocinnamonitrile, 50 ml. of chloroform, and 30 ml. of 3 N aqueous hydrochloric acid is stirred overnight at 25° C. After 15 hours the layers are separated and the chloroform phase is dried over sodium sulfate, and filtered through a pad of magnesol. The product is crystallized directly from the filtrate to provide 4.3 g. of colorless solid.

Similarly prepared is 3,5-dimethoxybenzoylacetonitrile; 3,4,5-trimethoxybenzoylacetonitrile and 2,4,6-trimethylbenzoylacetonitrile.

EXAMPLE 55

2-(3,4-Difluorobenzoyl)-3-hydroxycrotononitrile

A solution of 10.2 g. of 3,4-difluorobenzoylacetonitrile, 9.2 g. of triethyl orthoacetate and 20 ml. of acetic anhyride is heated on a steam bath for 0.5 hour and then poured into 200 ml. of water which is then heated on the steam bath for 2 hours. On cooling, the solid is filtered and then dissolved in methylene chloride. This solution is extracted with two portions of aqueous sodium bicarbonate and the aqueous extracts are combined and acidified with concentrated hydrochloric acid. The precipitate is extracted into methylene chloride, passed through a pad of Magnesol ®, heated and diluted with hexane. Upon cooling, colorless crystals result, yielding the title compound, m.p. 51°–54° C.

Similarly prepared are 2-(2,5-difluorobenzoyl)-3-hydroxycrotononitrile, 2-(3,4,5-trimethoxybenzoyl)-3-hydroxycrotononitrile, 2-(2,4,6-trimethylbenzoyl)-3-hydroxycrotononitrile, and 2-(2,5-dichlorobenzoyl)-3-hydroxycrotononitrile.

EXAMPLE 56

2-(Pentafluorobenzoyl)-3-hydroxycrotononitrile

A mixture of 6.8 g. of cyanoacetone, sodium salt in 70 ml. of dry tetrahydrofuran is cooled in ice and 5.0 g. of pentafluorobenzoyl chloride diluted to 10 ml. with tetrahydrofuran is added dropwise. The reaction is stirred overnight and then the solvent is evaporated. The residue is acidified and extracted into chloroform. This chloroform phase is then extracted with aqueous sodium bicarbonate which in turn is acidified and the colorless precipitate is again extracted with chloroform. Upon evaporation of the solvent, a yellow semi-solid results which is recrystallized from ethyl ether (−78° C.) to afford off-white crystals, m.p. 62°–63° C.

Similarly prepared is 2-(2-chloro-6-fluorobenzoyl)-3-hydroxycrotononitrile.

EXAMPLE 57

Cis-2-(p-fluorobenzoyl)-3-hydroxycrotononitrile

A mixture of 1.0 g. (9.5 mmole) of cyanoacetone, sodium salt in 20 ml. of tetrahydrofuran is stirred at room temperature as a solution of 0.37 ml. (3.2 mmole) of p-fluorobenzoyl chloride in 5 ml. of tetrahydrofuran is added. The reaction is heated to reflux for 2 hours and the solvent is then evaporated. The residue is acidified and extracted with diethyl ether. Evaporation of the organic phase provides 0.7 g. of a yellow oil which crystallizes on standing to provide the title compound.

EXAMPLE 58

2-(p-Fluorobenzoyl)-3-methoxycrotononitrile

A solution containing 55.8 g. (0.34 mole) of p-fluorobenzoylacetonitrile, 41 g. (0.34 mole) of trimethyl orthoacetate, and 90 g. (0.88 mole) of acetic anhydride is heated to reflux for 5 hours. The excess solvent and volatile by-products are then removed by vacuum distillation and the residue is recrystallized from diethyl ether. Alternatively, the distillation residue may be distilled over on a Kugelrohr apparatus at 160° C./0.25 mm. to provide a viscous oil which may be crystallized from diethyl ether to provide the pure title compound.

EXAMPLE 59

Cis-2-(p-fluorobenzoyl)-3-hydroxycrotononitrile

A solution of 5 g. of cis-2-(p-fluorobenzoyl)-3-methoxycrotononitrile in 50 ml. of ethanol is treated with 25 ml. of 3 N aqueuos hydrochloric acid at room temperature for one hour. The solvent is evaporated, the residue diluted with water, and the product is extracted with chloroform. The organic phase is separated, dried, filtered and evaporated to provide the title compound.

EXAMPLE 60

2-(Dimethylaminomethylene)-2-(p-fluorophenyl)-butane-1,3-dione

A solution of 15 g. of p-fluorobenzoylacetone in 35 ml. of N,N-dimethylformamide dimethylacetal is heated on a steam bath and the volatile by-product (methanol) is distilled out. When the theoretical amount of methanol has been collected, the reaction mixture is pumped dry, then the product is collected by distillation from the reaction pot at 150° C./0.025 mm. Crystalline product (19.5 g., 97% yield) is thus obtained upon cooling of the distillate.

EXAMPLE 61

4-Acetyl-5-(p-fluorophenyl)isoxazole and 4-(p-fluorobenzoyl)-5-methylisoxazole

To a solution of 12.8 g. of 2-(dimethylaminomethylene)-1-(p-fluorophenyl)butane-1,3-dione in 130 ml. of THF is added 4.10 g. of hydroxylamine hydrochloride, followed by 40 ml. of water. The reaction is heated to reflux for 2 hours, then cooled and the solvent is evaporated. The residue is partitioned between ether and water and the organic layer is separated and evaporated. The residue is distilled at 100°-110° C./0.25 mm. to provide 9.0 g. of an oily mixture of approximated equal amounts of 4-(p-fluorobenzoyl)-5-methylisoxazole and 4-acetyl-5-(p-fluorophenyl)isoxazole.

EXAMPLE 62

Cis-2-(p-fluorobenzoyl)-3-hydroxycrotononitrile

A solution of 1.65 g. of a mixture of 4-acetyl-5-(p-fluorophenyl)isoxazole and 4-(p-fluorobenzoyl)-5-methylisoxazole in equal amounts is dissolved in 7 ml. of methanol and treated with 5 ml. of 10% aqueous sodium hydroxide. The solution is heated on a steam bath for 15 minutes then cooled, acidified with 1 N aqueous HCl and extracted with ether. Evaporation of the ether provides 1.55 g. of product. Recrystallization from isopropanol provides 1.0 g. (66%) of cis-2-(p-fluorobenzoyl)-3-hydroxycrotononitrile.

EXAMPLE 63

3-Amino-2-(p-fluorobenzoyl)crotononitrile

Approximately 50 ml. of liquid ammonia is condensed in a three-neck flask cooled to −78° in a dry ice-acetone bath. To this is added 200 mg. of sodium metal, followed by 100 mg. of ferric chloride hexahydrate. When the blue color had vanished, 6.2 g. of 2-(p-fluorobenzoyl)-3-methoxycrotononitrile is added. After stirring for one hour, the reaction is allowed to warm and the solvent evaporate. The residue is dissolved in hot ethyl acetate and filtered through Celite ®. The filtrate is concentrated on the steam bath and diluted with hexane. Upon cooling, the crystalline product precipitates, is filtered and dried.

EXAMPLE 64

2-(p-Fluorobenzoyl)-3-methylaminocrotononitrile

In the glass liner of a stainless steel bomb cooled to −78° is condensed 10 ml. of methylamine. To this is added 0.5 ml. of 2 M n-butyllithium (in hexane), followed by 5.0 g. of 2-(p-fluorobenzoyl)-3-methoxycrotononitrile. The bomb is sealed and heated on a steam bath overnight. The bomb is then cooled, opened and the contents evaporated. The residue is dissolved in chloroform, passed through a Magnesol ® pad and the filtrate is evaporated. The residue is recrystallized from chloroform-hexane yielding the title compound.

EXAMPLE 65

2-(p-Fluorobenzoyl)-3-butylaminocrotononitrile

A sample of 2.5 g. of 2-(p-fluorobenzoyl)-3-methoxycrotononitrile is dissolved in 10 ml. of n-butylamine. The solution is sealed in a stainless steel bomb and heated on a steam bath overnight. The bomb is then opened and the solvent evaporated under reduced pressure. A greenish oil is obtained which is distilled on a Kugelrohr apparatus at 200° C./0.1 mm. to obtain the yellow oily product.

EXAMPLE 66

2-(p-Fluorobenzoyl)-3-dimethylaminocrotononitrile

To a solution of 14.5 g. (0.10 m) of (p-fluorobenzoyl)acetonitrile in 100 ml. of chloroform, cooled in an ice-salt bath, was added 13.3 g. (0.1 m) of N,N-dimethylacetamide dimethylacetal in 20 ml. chloroform. The reaction mixture was stirred in the ice-salt bath for 2 hours, then evaporated in vacuo to an orange oil. The oil was dissolved in 150 ml. benzene and passed through Magnesol ®. The filtrate was evaporated and the oil thus obtained was dissolved in 50 ml. benzene to which petroleum ether was added until the solution became cloudy. The precipitate which formed upon cooling was collected. The solid was recrystallized twice from benzene-petroleum ether, with charcoal treatment to yield 5.8 g. (27%) of light yellow crystals, m.p. 90°–92° C.

EXAMPLE 67

2-(p-Fluorobenzoyl)-3-hydroxycrotononitrile

A solution of 1.35 g. (0.006 m) of 2-(p-fluorobenzoyl)-3-dimethylaminocrotononitrile in a mixture of 15 ml. methanol and 8 ml. of 1 N HCl was heated on the steam bath in an open beaker for 45 minutes. Upon cooling in an ice bath, a solid formed, was collected, and then recrystallized from cyclohexane-petroleum ether with charcoal treatment, giving 0.7 g. (64%) of light pinkish crystals, m.p. 65°–67° C.

EXAMPLE 68

2-(p-Fluorobenzoyl)-3-methoxy-2-pentenonitrile

A solution containing 30 g. of (p-fluorobenzoyl)acetonitrile, 36.4 g. of trimethylorthopropionate and 57 g. of acetic anhydride is heated in an oil bath at 130° for 3 hours. The ethanol and excess acetic anhydride is distilled off and the residue is diluted with chloroform. The chloroform solution is passed quickly through Magnesol ® and concentrated, then cooled to produce the title product.

EXAMPLE 69

2-(p-Fluorobenzoyl)-3-hydroxy-2-pentenonitrile

A two-phase mixture of 5.0 g. 2-(p-fluorobenzoyl)-3-methoxy-2-pentenonitrile in 50 ml. of chloroform is stirred with a 50 ml. solution of aqueous 1 N hydrochloric acid. After 24 hours, the organic phase is separated and evaporated. The residue is recrystallized from chloroform to yield the title compound.

EXAMPLE 70

2-(p-Fluorobenzoyl)-3-N-piperidylcrotononitrile

To a solution of 5.0 g. of 2-(p-fluorobenzoyl)-3-methoxycrotononitrile in 50 ml. of dry tetrahydrofuran is added 5 ml. of piperidine. The reaction is heated to reflux for 2 hours, cooled and evaporated in vacuo. The residue is recrystallized from chloroform/hexane to provide the crystalline title compound.

EXAMPLE 71

2-(p-Fluorobenzoyl)-3-diethylaminocrotononitrile

A volume of 10 ml. of diethylamine is condensed in a glass tube at $-78°$ C. A sample of 5 g. of 2-(p-fluorobenzoyl)-5-methoxycrotononitrile is added, the tube is sealed in a stainless steel bomb and heated on a steam bath overnight. The bomb is then cooled, opened, and the contents evaporated. The residue was recrystallized from chloroform to provide the title compound.

EXAMPLE 72

2-(p-Fluorobenzoyl)-3-hydroxycrotononitrile, sodium salt

A solution of 5.0 g. of 2-(p-fluorobenzoyl)-3-hydroxycrotononitrile in 30 ml. of dry tetrahydrofuran is added dropwise to a stirred suspension of sodium hydride (1.0 g.) in 30 ml. of dry tetrahydrofuran. After the addition is complete, the reaction mixture is stirred for 2 hours and the resulting orange solution is poured into diethyl ether. A colorless solid precipitates which is filtered and dried to provide the title compound.

EXAMPLE 73

2-(p-Fluorobenzoyl)-3-hydroxycrotononitrile, triethylammonium salt

A solution of 1.3 ml. of triethyl amine in 10 ml. of diethyl ether is added dropwise to a solution of 1.5 g. of 2-(p-fluorobenzoyl)-3-hydroxycrotononitrile in 20 ml. of diethyl ether. After stirring for 1 hour, a yellow oil separated which crystallizes upon evaporation of the solvent. The product was filtered, washed with ether and dried, providing the title compound.

We claim:

1. A compound selected from the group consisting of those of the formula:

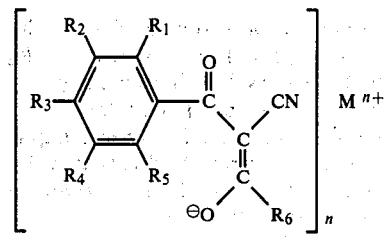

wherein $R_1$, $R_2$, $R_3$, $R_4$ and $R_5$ are each individually selected from the group consisting of hydrogen, halogen, alkyl having from 1 to 4 carbon atoms, alkoxy having from 1 to 4 carbon atoms, trifluoromethyl and trichloromethyl with the proviso that at least two of $R_1$, $R_2$, $R_3$, $R_4$ and $R_5$ must be hydrogen but $R_1$, $R_2$, $R_3$, $R_4$ and $R_5$ may not all be hydrogen; $R_6$ is alkyl having from 1 to 4 carbon atoms; n is an integer from 1 to 3 and M is hydrogen or a pharmaceutically acceptable cation; and the tautomers thereof.

2. The compound according to claim 1 wherein M is hydrogen, n is 1, $R_3$ is fluoro, $R_1$, $R_2$, $R_4$ and $R_5$ are all hydrogen, and $R_6$ is methyl; cis-2-(p-fluorobenzoyl)-3-hydroxycrotononitrile.

3. The compound according to claim 1 wherein M is hydrogen, n is 1, $R_3$ is chloro, $R_1$, $R_2$, $R_4$ and $R_5$ are all hydrogen, and $R_6$ is methyl; cis-2-(p-chlorobenzoyl)-3-hydroxycrotononitrile.

4. The compound according to claim 1 wherein M is hydrogen, n is 1, $R_1$ is chloro, $R_2$, $R_3$, $R_4$ and $R_5$ are all hydrogen and $R_6$ is methyl; cis-2-(o-chlorobenzoyl)-3-hydroxycrotononitrile.

5. The compound according to claim 1 wherein M is hydrogen, n is 1, $R_2$ is fluoro, $R_1$, $R_3$, $R_4$ and $R_5$ are all hydrogen, and $R_6$ is methyl; cis-2-(m-fluorobenzoyl)-3-hydroxycrotononitrile.

6. The compound according to claim 1 wherein M is hydrogen, n is 1, $R_3$ is trifluoromethyl, $R_1$, $R_2$, $R_4$ and $R_5$ are all hydrogen and $R_6$ is methyl; cis-3-hydroxy-2-($\alpha,\alpha,\alpha$-trifluoro-p-toluoyl)-crotononitrile.

7. The compound according to claim 1 wherein M is hydrogen, n is 1, $R_3$ is methoxy, $R_1$, $R_2$, $R_4$ and $R_5$ are all hydrogen, $R_6$ is methyl; cis-2-(p-anisoyl)-2-hydroxycrotononitrile.

8. The compound according to claim 1 wherein M is hydrogen, n is 1, $R_1$ is fluoro, $R_2$, $R_3$, $R_4$ and $R_5$ are all hydrogen, $R_6$ is methyl; cis-2-(o-fluorobenzoyl)-3-hydroxycrotononitrile.

9. The compound according to claim 1 wherein M is hydrogen, n is 1, $R_1$ is methoxy, $R_2$, $R_3$, $R_4$ and $R_5$ are all hydrogen, $R_6$ is methyl; cis-3-hydroxy-2-(p-toluoyl)-crotononitrile.

10. The compound according to claim 1 wherein M is hydrogen, n is 1, $R_3$ is methyl, $R_1$, $R_2$, $R_4$, and $R_5$ are all hydrogen, $R_6$ is methyl; cis-3-hydroxy-2-(p-toluoyl)-crotononitrile.

11. The compound according to claim 1 wherein M is hydrogen, n is 1, $R_1$ is methyl, $R_2$ is chloro, $R_3$, $R_4$ and $R_5$ are all hydrogen, $R_6$ is methyl; cis-2-(3-chloro-o-toluoyl)-3-hydroxycrotononitrile.

12. The compound according to claim 1 wherein M is hydrogen, n is 1, $R_3$ is bromo, $R_1$, $R_2$, $R_4$ and $R_5$ are all hydrogen, $R_6$ is methyl; cis-2-(p-bromobenzoyl)-3-hydroxycrotononitrile.

13. The compound according to claim 1 wherein M is sodium, n is 1, $R_3$ is fluoro, $R_1$, $R_2$, $R_4$ and $R_5$ are all hydrogen; cis-2-(p-fluorobenzoyl)-3-hydroxycrotononitrile, sodium salt.

14. The compound according to claim 1 wherein M is triethylammonium, n is 1, $R_3$ is fluoro, $R_1$, $R_2$, $R_4$ and $R_5$ are all hydrogen; cis-2-(p-fluorobenzoyl)-3-hydroxycrotononitrile, triethylammonium salt.

15. A compound selected from the group consisting of cis-2-pentafluorobenzoyl-3-hydroxycrotononitrile, the tautomers thereof, and the pharmacologically acceptable cationic salts thereof.

16. The method of inhibiting the progression of arthritis in a mammal which comprises administering to said mammal an effective amount of a compound selected from the group consisting of those of the formula:

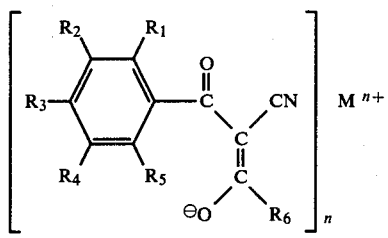

wherein $R_1$, $R_2$, $R_3$, $R_4$ and $R_5$ are each individually selected from the group consisting of hydrogen, halogen, alkyl having from 1 to 4 carbon atoms, alkoxy having from 1 to 4 carbon atoms, trifluoromethyl and trichloromethyl with the proviso that at least two of $R_1$, $R_2$, $R_3$, $R_4$ and $R_5$ must be hydrogen but $R_1$, $R_2$, $R_3$, $R_4$ and $R_5$ may not all be hydrogen; $R_6$ is alkyl having from 1 to 4 carbon atoms; n is an integer from 1 to 3 and M is hydrogen or a pharmaceutically acceptable cation; and the tautomers thereof.

17. The method of inhibiting progressive joint deterioration in a mammal which comprises administering to said mammal an effective amount of a compound selected from the group consisting of those of the formula:

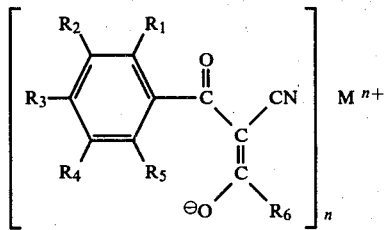

wherein $R_1$, $R_2$, $R_3$, $R_4$ and $R_5$ are each individually selected from the group consisting of hydrogen, halogen, alkyl having from 1 to 4 carbon atoms, alkoxy having from 1 to 4 carbon atoms, trifluoromethyl and trichloromethyl with the proviso that at least two of $R_1$, $R_2$, $R_3$, $R_4$ and $R_5$ must be hydrogen but $R_1$, $R_2$, $R_3$, $R_4$ and $R_5$ may not all be hydrogen; $R_6$ is alkyl having from 1 to 4 carbon atoms; n is an integer from 1 to 3 and M is hydrogen or a pharmaceutically acceptable cation; and the tautomers thereof.

18. The method of meliorating inflammation in a mammal which comprises administering to said mammal an effective amount of a compound selected from the group consisting of those of the formula:

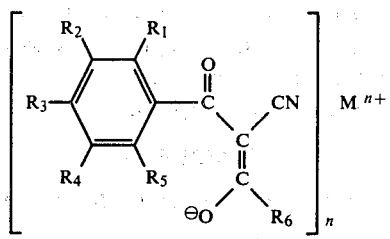

wherein $R_1$, $R_2$, $R_3$, $R_4$ and $R_5$ are each individually selected from the group consisting of hydrogen, halogen, alkyl having from 1 to 4 carbon atoms, alkoxy having from 1 to 4 carbon atoms, trifluoromethyl and trichloromethyl with the proviso that at least two of $R_1$, $R_2$, $R_3$, $R_4$ and $R_5$ must be hydrogen but $R_1$, $R_2$, $R_3$, $R_4$ and $R_5$ may not all be hydrogen; $R_6$ is alkyl having from 1 to 4 carbon atoms; n is an integer from 1 to 3 and M is hydrogen or a pharmaceutically acceptable cation; and the tautomers thereof.

19. An anti-arthritic composition in dosage unit form useful for meliorating the inflammation and/or the progressive joint deterioration characteristic of arthritic disease in mammals comprising from about one milligram to about 250 milligrams per kilogram of body weight per dosage unit of a compound selected from the group consisting of those of the formula:

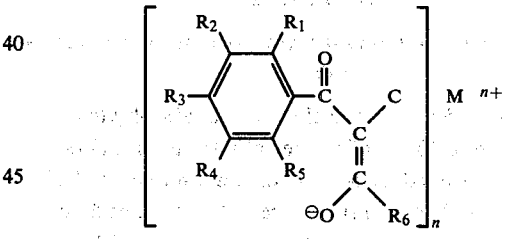

wherein $R_1$, $R_2$, $R_3$, $R_4$ and $R_5$ are each individually selected from the group consisting of hydrogen, halogen, alkyl having from 1 to 4 carbon atoms, alkoxy having from 1 to 4 carbon atoms, trifluoromethyl and trichloromethyl with the proviso that at least two of $R_1$, $R_2$, $R_3$, $R_4$ and $R_5$ must be hydrogen but $R_1$, $R_2$, $R_3$, $R_4$ and $R_5$ may not all be hydrogen; $R_6$ is alkyl having from 1 to 4 carbon atoms; n is an integer from 1 to 3 and M is hydrogen or a pharmaceutically acceptable cation; and the tautomers thereof; in association with a pharmaceutical carrier.

* * * * *